United States Patent [19]
Whiteside et al.

[11] Patent Number: 5,879,393
[45] Date of Patent: Mar. 9, 1999

[54] TRIAL FEMORAL PROSTHESIS FOR USE IN KNEE JOINT REPLACEMENT SURGERY

[75] Inventors: Leo A. Whiteside, Bridgeton, Mo.;
Jason D. Blain, Palm Desert, Calif.;
Thomas A. Carls, Memphis, Tenn.;
Chris E. Johnson, Memphis, Tenn.;
Anthony J. Melkent, Memphis, Tenn.;
Paul Wheeler, Walls, Miss.

[73] Assignee: Smith & Nephew, Inc., Memphis, Tenn.

[21] Appl. No.: 861,094

[22] Filed: May 21, 1997

[51] Int. Cl.$^6$ .................................. A61F 2/38; A61F 2/48
[52] U.S. Cl. ................................. 623/20; 606/88
[58] Field of Search .................................. 623/16, 18, 20; 606/80, 86, 87, 88, 89

[56] References Cited

U.S. PATENT DOCUMENTS

| | | | |
|---|---|---|---|
| 5,258,032 | 11/1993 | Bertin | 623/20 |
| 5,417,693 | 5/1995 | Sowden et al. | 606/85 |
| 5,458,645 | 10/1995 | Bertin | 623/20 |
| 5,462,550 | 10/1995 | Dietz et al. | 606/86 |
| 5,702,460 | 12/1997 | Carls et al. | 623/20 |

FOREIGN PATENT DOCUMENTS 0303467  2/1989  European Pat. Off. ............... 623/20

*Primary Examiner*—David Isabella
*Attorney, Agent, or Firm*—Pravel, Hewitt & Kimball

[57] ABSTRACT

A posterior stabilized femoral trial apparatus for preparing a patient's femur to receive a posterior stabilized femoral prosthesis includes a trial body with proximal and distal portions, the distal portion having an articulating surface for articulating with a patient's tibial component. A module fits the trial body at the proximal surface, the module being selected from a kit or group of modules of differing sizes and shapes. The module includes a rasping surface that extends longitudinally. The trial body includes cutting surfaces at the posterior condyles. The module is removably attachable to the trial body at the proximal surface. During use, the apparatus of the present invention enables the surgeon to resect the patient's femur in a revision surgical case using the trial itself and more particularly the rasping surface and cutting surface thereon.

26 Claims, 4 Drawing Sheets

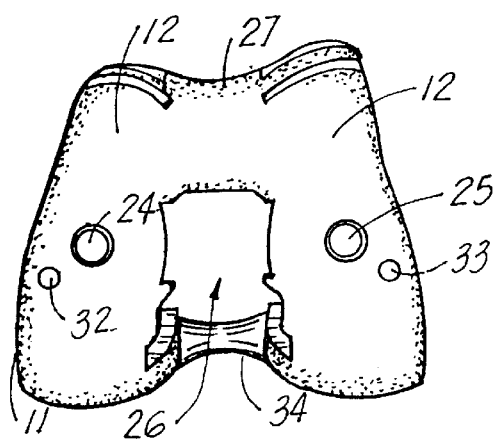
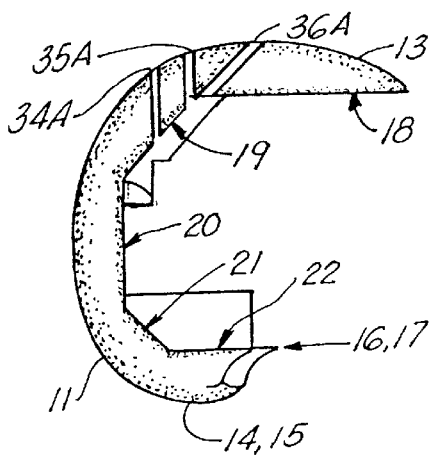
FIG. 3
FIG. 4
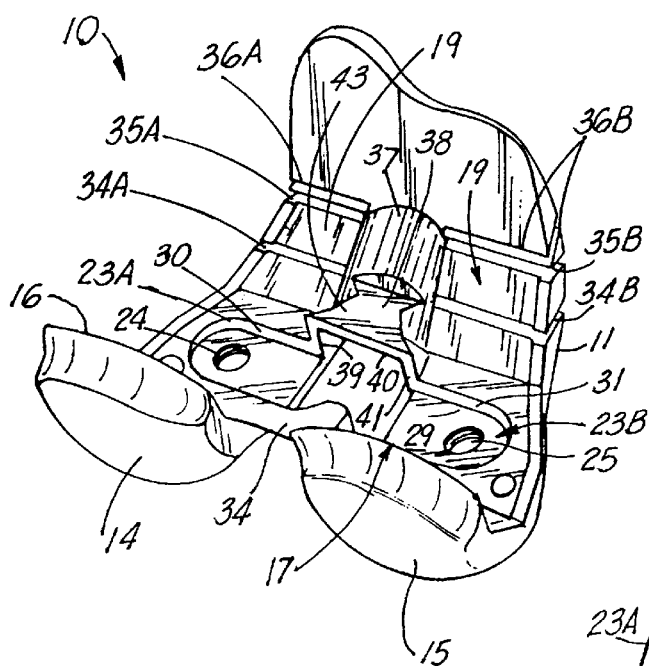
FIG. 1
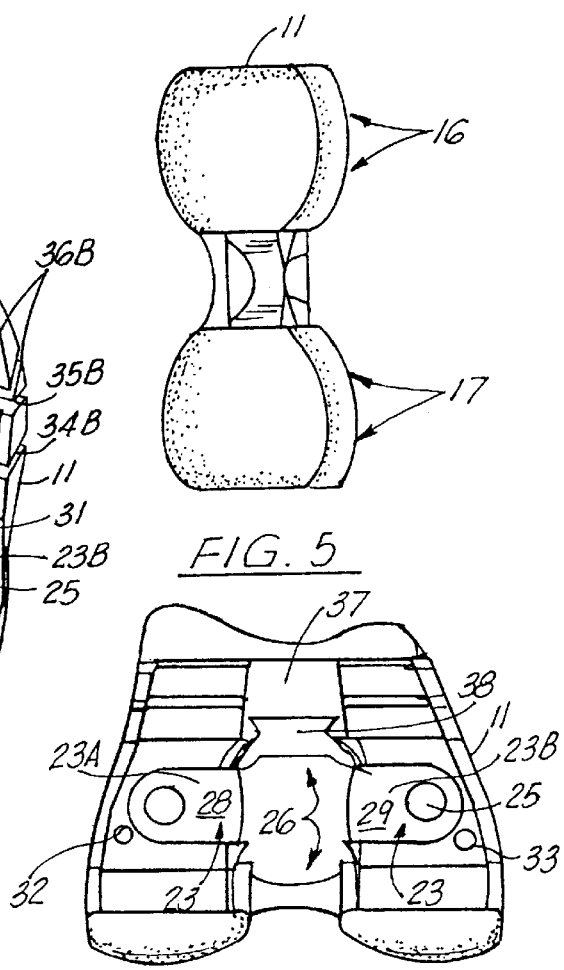
FIG. 5
FIG. 2

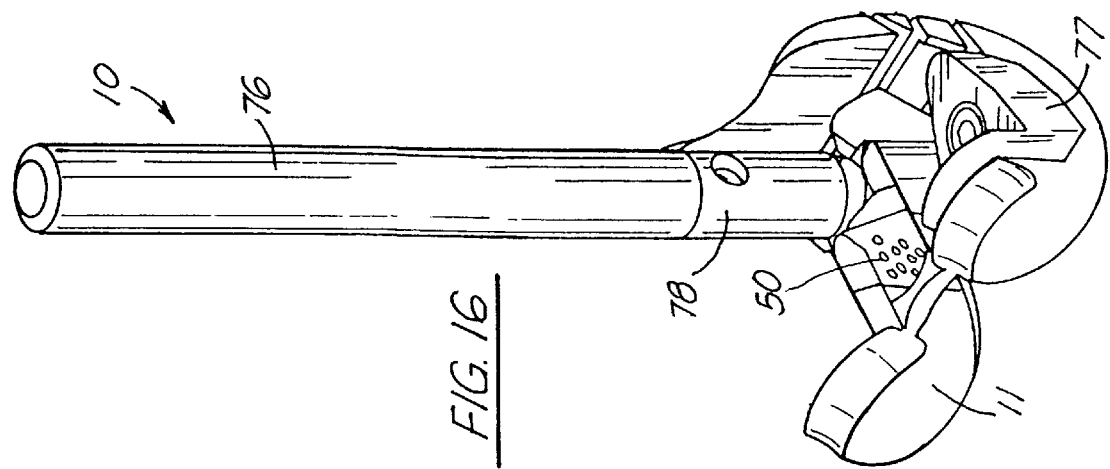
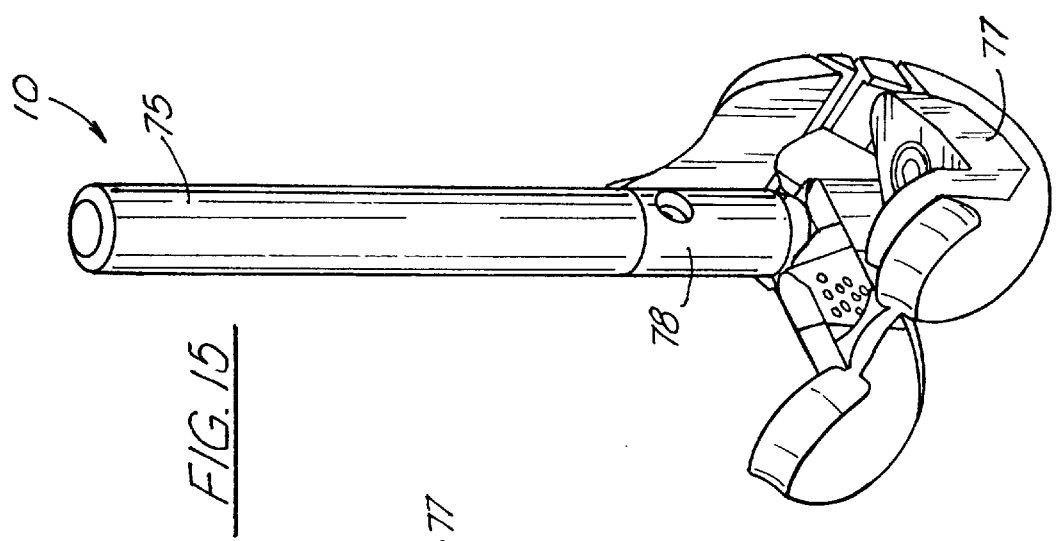
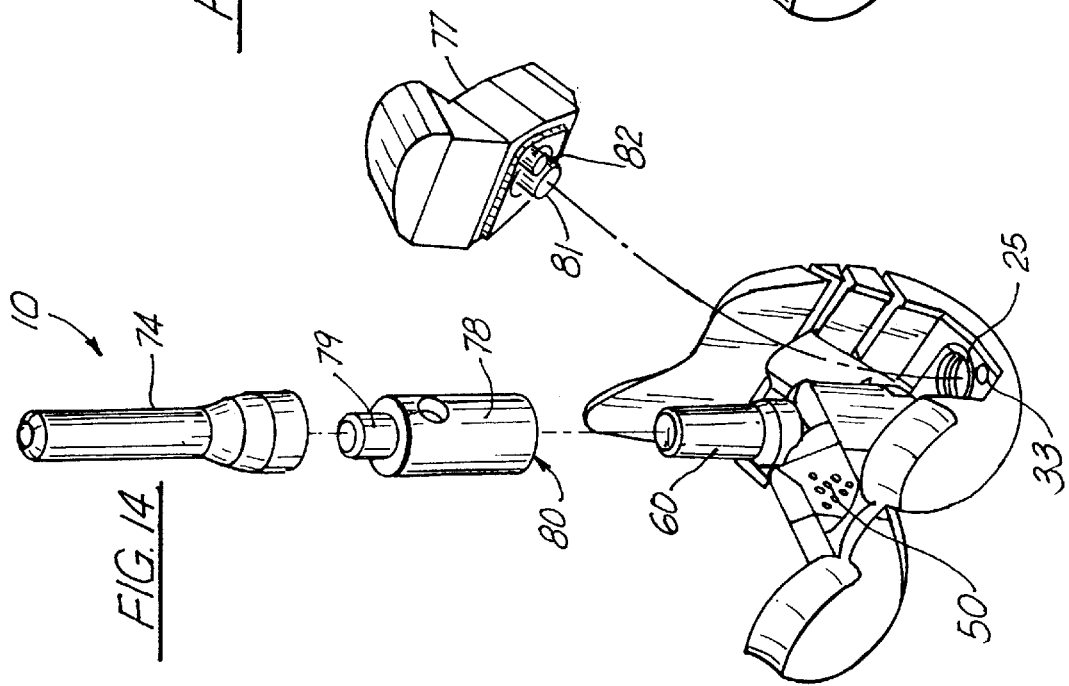

TRIAL FEMORAL PROSTHESIS FOR USE IN KNEE JOINT REPLACEMENT SURGERY

BACKGROUND OF THE INVENTION

1. Field of the Invention

The present invention relates to orthopedic surgical instrumentation, and more particularly to an improved femoral trial prosthesis apparatus having particular utility in knee joint replacement surgery (particularly revision surgical cases) wherein a previous femoral prosthesis has been removed by a surgeon. Even more particularly, the present invention relates to an improved posterior stabilized-type femoral trial apparatus for preparing a patient's femur to receive a posterior stabilized femoral prosthesis wherein a trial body carries a module selected from a kit of modules, each module including cutting and rasping surfaces that extend longitudinally and a stem portion for accepting a stem member from a kit of various stem members of differing sizes and diameters.

2. General Background of the Invention

When a surgeon removes a previous femoral implant, it is known in the art as a "revision" case. A surgeon must remove that previous femoral implant and replace it with a new implant. However, often the patient has weakened or reduced bone tissue for attachment.

In the case of revision femoral implant surgery, surgeons often use a posterior stabilized-type femoral implant. Such a posterior stabilized femoral implant is sold by Smith & Nephew of Memphis, Tennessee as part of the Genesis Total Knee System or the Profix Total Knee System.

The surgeon may attempt to use a trial prosthesis to first determine the appropriate size and shape of the final prosthesis to be implanted.

BRIEF SUMMARY OF THE INVENTION

The present invention provides a posterior stabilized femoral trial that resects the bone in the distal end of the femur to prepare the posterior stabilized box housing as the trial is driven into place. The present invention provides a posterior stabilized femoral trial apparatus for preparing a patient's femur to receive a posterior stabilized femoral prosthesis. The apparatus of the present invention includes a trial body that has proximal and distal portions, the distal portion of the trial body having an articulating surface that articulates with a patient's tibial component or with a patient's tibia.

The femoral articulating surface includes anterior, distal, and posterior condylar portions.

The trial body also has a proximal surface that includes a plurality of flat intersecting surfaces, preferably five (5) of such flat intersecting surfaces.

The present invention provides a module that fits the trial body at the proximal surface, the module including a rasping surface that extends longitudinally along a proximal to distal plane that is generally parallel to an anterior to posterior plane.

The module is removably attachable to the trial body at the proximal surface.

The apparatus includes portions that extend laterally on a medial to lateral line, attaching to the medial and lateral sides of the trial body. A slot on the distal surface of the trial body receives the module.

Cutting surfaces are provided on the trial body at the condylar surfaces.

A plurality of cutting guide slots extend from the proximal to the distal surface of the body and along medial and lateral lines. There are preferably three sets of cutting guide slots including distal cutting guide slots and anterior chamfer cutting guide slots.

An opening of the trial body is placed in between the condylar portions and extends anteriorly a partial distance toward the anterior portion of the trial body, the opening being bordered on the rear by a transverse bar that spans in between the condylar portions.

Fasteners enable the module to be attached to and removed from the trial body.

The module includes a pair of flange portions that engage the body, the flange portions having openings through which threaded fasteners can be placed for attaching the module to the trial body.

The trial body includes a projecting portion that extends away from the flange portion along a generally proximal to distal line.

The module includes a frustoconically-shaped projecting portion that can receive a selected stem extension, a kit being provided with several stem extensions of differing lengths and diameters. The module includes wall portions, at least one of which has a rasping surface thereon. In the preferred embodiment, the lateral wall portion carries the rasping surface.

In the preferred embodiment, the stem connector forms an angle of less than ninety degrees (90°) with the plane of the flange portions thus providing a valgus adjustment for the stem connector and stem extensions when the trial prosthesis is then placed on the patient's distal femur.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 1 is a perspective view of the preferred embodiment of the apparatus of the present invention illustrating the trial prosthesis body portion thereof;

FIG. 2 is a proximal view of the preferred embodiment of the apparatus of the present invention illustrating the trial prosthesis body;

FIG. 3 is a distal view of the preferred embodiment of the apparatus of the present invention illustrating the trial prosthesis body;

FIG. 4 is a side view of the preferred embodiment of the apparatus of the present invention illustrating the trial prosthesis body;

FIG. 5 is a posterior view of the preferred embodiment of the apparatus of the present invention illustrating the trial prosthesis body;

FIGS. 14–16 are perspective views of the preferred embodiment of the apparatus of the present invention shown with a trial coupler, trial stems of differing lengths, and trial wedge.

DETAILED DESCRIPTION OF THE INVENTION

Figure 6:
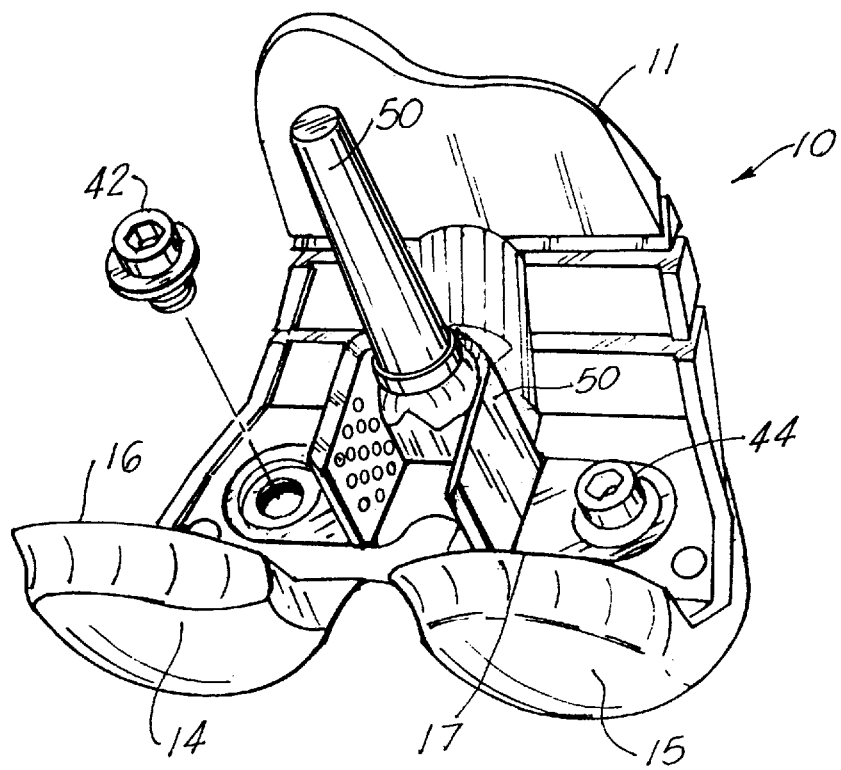
FIG. 6 is a perspective view of the preferred embodiment of the apparatus of the present invention illustrating the trial prosthesis body and a selected posterior stabilized module.
Figure 7:
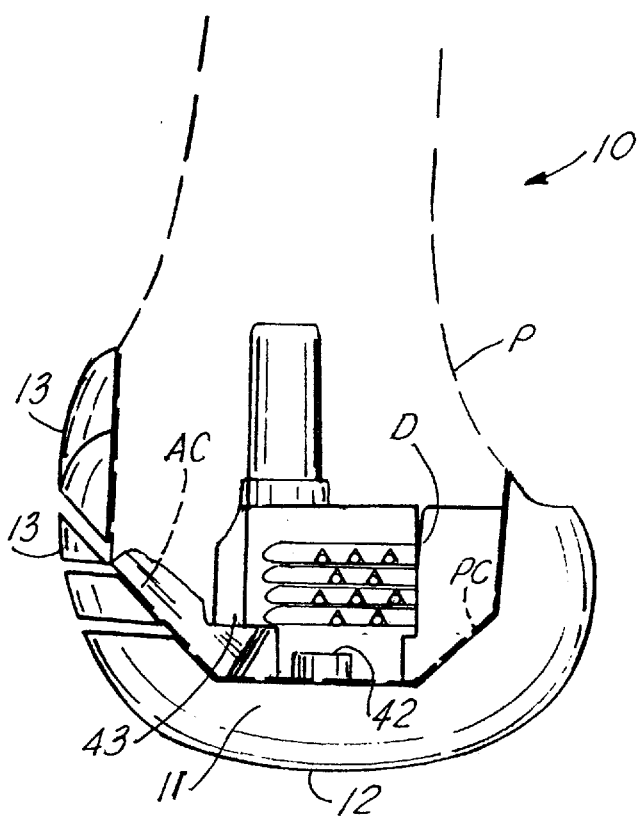
FIG. 7 is a side view of the preferred embodiment of the apparatus of the present invention shown after placement on a patient's distal femur that is shown in phantom lines.
Figure 8:
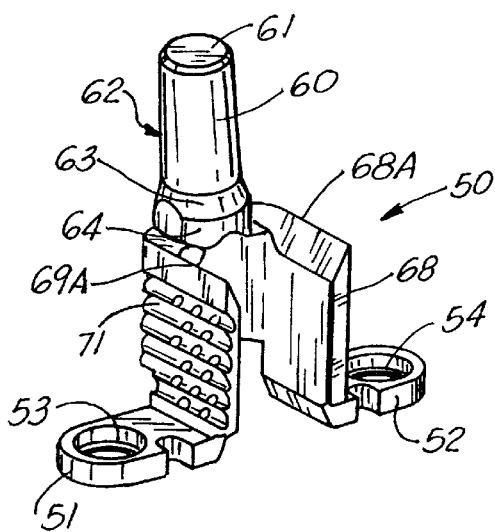
FIG. 8 is a partial perspective view of the preferred embodiment of the apparatus of the present invention illustrating the module portion thereof.
Figure 9:
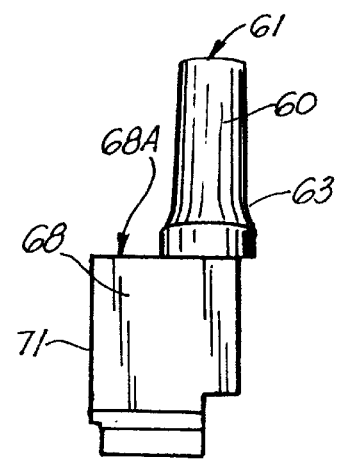
FIG. 9 is a side view of the module of FIG. 8.
Figure 10:
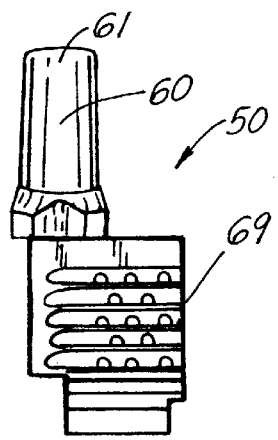
FIG. 10 is another side view of the module of FIG. 8 showing the lateral side thereof.

FIGS. 1–7 show the preferred embodiment of the apparatus of the present invention designated by the numeral 10 in FIGS. 6–7.

Femoral trial apparatus 10 includes a trial body 11 (FIGS. 1–7) having a distal surface 12 that includes various articulating portions including an anterior articulating surface 13, condylar surfaces 14, 15, and cutting edges 16, 17 at the condylar surfaces 14, 15.

Trial body 11 can provide a plurality of five flat surfaces 18, 19, 20, 21, 22 that are used to form a load transfer interface with a patient's surgically prepared femur F. The femur F is surgically prepared as shown in FIG. 7 to provide five cut surfaces. These surgically cut surfaces on femur F correspond in shape and placement to the surfaces 18, 19, 20, 21, and 22 of trial body 11.

When the femur F is surgically cut (see FIG. 7), the surgeon forms a plurality of five cut surfaces including: a distal D cut surface, anterior A and posterior P cut surfaces, and anterior and posterior chamfer cut surfaces AC, PC. When a surgeon performs a revision surgical case, these cut surfaces are already present on the femur from a previous surgery. When the surgeon removes the previous implant in a revision case, the femur F resembles the shape shown in phantom lines in FIG. 7. The surgeon then uses the trial apparatus 10 to reshape the distal femur F and to determine the correct size for a final prosthesis to be used in the revision surgery, replacing the old removed implant. The five surgically prepared surfaces are reshaped somewhat using trial body 11. The cutting surfaces 16, 17 shave bone from the posterior condylar cut surface P of the femur F. Cutting edges 68A & 69A and rasping surface 71 on the module 50 also cut and shave bone.

In FIG. 1, a slot or recess 23 is provided for receiving a module 50. The module 50 is shown in FIGS. 8–13. The module 50 is assembled to implant body 11 in FIGS. 6–7. Implant body 10 provides a pair of spaced apart openings 24, 25. An opening or open space 26 as shown in FIG. 2 is provided in between the recess portions 23A, 23B.

In FIG. 3, anterior groove 27 extends along the anterior portion of trial body 11, copying the shape of the femoral prosthesis to be used after the trial 10 has been employed by the surgeon to arrive at a correct size. Each recessed portion 23A, 23B provides a flat surface 28, 29 respectively. Each flat surface 28, 29 is surrounded respectively by a sidewall portion 30, 31.

Holes 32, 33 are provided at flat surface 20 for providing alignment with module 50 at correspondingly shaped openings 72, 73 of module 50. Post 34 spans between condylar portions 14, 15. Holes 32, 33 receive a correspondingly shaped peg 82 on a trial wedge 77. Threaded fastener 81 of wedge 77 fits threaded opening 24 or 25 (see FIG. 14).

A plurality of cutting guide slots are provided for cutting bone tissue at the patient's distal femur. Often bone is missing from the femur in the distal area. Bone has often been worn or eroded away in revision cases. The surgeon cleans up by cutting some bone from either the medial or lateral distal surface using a selected cutting guide slot 34A, 34B, 35A, 35B, 36A, 36B. Cutting guide slots 34A and 34B can be used to track and guide a cutting blade, saw, or the like during a cutting of tissue from the patient's distal femoral surface. Similarly, guide slots 35A, 35B guide a cutting blade during a cutting of the distal femur. The cutting guide slots 36A, 36B are chamfer cutting guide slots for making anterior chamfer cuts on the patient's distal femur.

Raised portions 37, 38 form a thickened reinforcement of trial body 11 at the cutting guide slots 34A, 35A, 36A and 34B, 35B, 36B. The raised portion 38 has a flat surface 43 for receiving the surface 58 of module 50. Raised portion 38 is defined by flat wall sections 39, 40, 41 (FIG. 1). Module 50 aligns with and abuts flat surfaces 39, 40, 41 of trial body 11. A generally rectangular slot 26 accepts module 50. Surface 58 of module 50 rests upon surface 43 of body 11.

As seen in FIGS. 6–7 and 14–16, module 50 attaches to trial body 11 using threaded fasteners 42, 44. The fasteners 42, 44 pass through respective openings 53, 54 of flanges 51, 52 and then threadably engage internally threaded openings 24, 25 respectively of trial body 11. If a trial wedge 77 is to be attached, a threaded fastener passes through an opening in the trial wedge and through the opening 53 or 54 of module 50 before forming a threaded attachment to an opening 24 or 25. If a trial wedge 77 is attached, the peg 82 of trial wedge 77 registers in slot 72 or 73 of module 50 and then into opening 32 or 33 of trial body 11.

The construction of module 50 is shown more particularly in FIGS. 8–13. Module 50 has a lower end portion 55 in the form of flanges 51, 52. Flange 51 has a flat surface 57 that fits surface 29 of the recess portion 23A of trial body 11. Flange 52 has a flat surface 56 that fits surface 28 of the recess portion 29 of trial body 11.

Module 50 has stem connector 60 with a flat surface 61 at the free end of stem 60. Stem 60 has a cylindrical base 64, tapered transition 63 and frustoconical surface 62 that enables a trial coupler 78 (see FIGS. 14–16) to preferably form a taper lock connection with stem 60 at surface 62.

Figure 11:
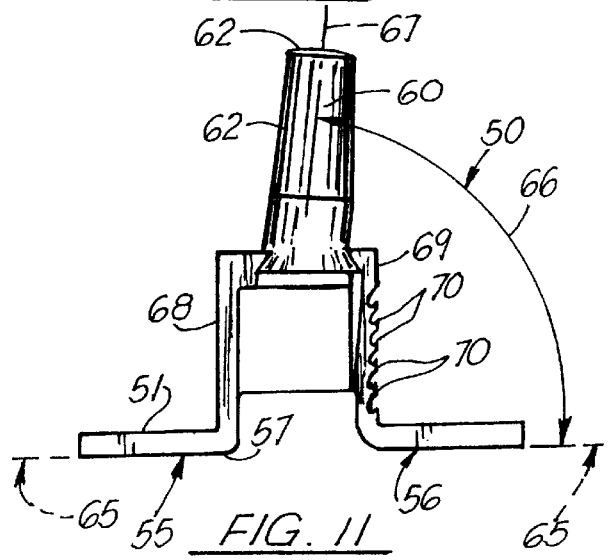
FIG. 11 is an anterior view of the module of FIGS. 8–10.
Figure 12:
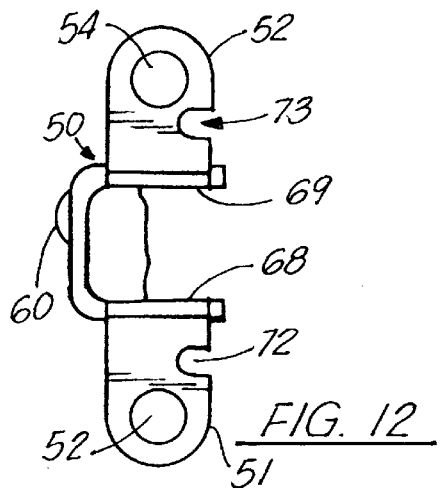
FIG. 12 is a distal view of the module of FIGS. 8–11.
Figure 13:
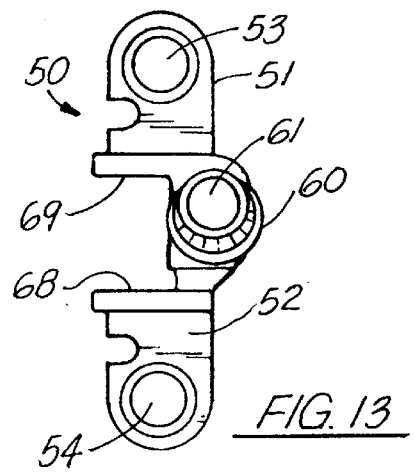
FIG. 13 is a proximal view of the module of FIGS. 8–12.

Trial coupler 78 can have upper projecting portion 79 that connects (e.g., a threaded connection) to a correspondingly threaded socket at the lower end of each stem 74, 75, 76. A selected stem extension 74, 75 or 76 could then be selectively connected to trial coupler 78 by a surgeon. In this manner, the trial prosthesis 10 of the present invention enables a surgeon to vary the length and diameter of the stem portion of a trial body when fitting the trial body 11 and an attached trial coupler and/or a selected stem extension 74, 75 or 76 to a patient's surgically prepared femur. Coupler 78 has a lowermost socket 80 that corresponds in size and shape to stem connector 60 so that a taper lock connection can be formed between stem connector 60 and socket 80. In FIG. 11, stem connector 60 is inclined with respect to a plane 65 defined by surfaces 56, 57. The inclination is indicated by arrow 66 in FIG. 11. Angle 66 can be between 80°–90° for example, enabling the central axis 67 of stem connector 60 to compensate for the valgus angle of the patient's intramedullary canal at the distal femoral region. Likewise, a generally cylindrically shaped stem extension 74, 75 or 76 affixed to connector 60 will form an angle 66 with the plane 65 of surfaces 56, 57. The surfaces 56, 57 register against flat surfaces 28, 29 of trial body 11. The surfaces 28, 29 are parallel to the surgically cut distal surface D of the patient's distal femur F (see FIG. 7). Also, the surfaces 28, 29 (and 56, 57) are parallel to surface 20 of implant body 11 that fits against the surgically cut distal surface D of femur 11.

Stem connector 60 attaches to flanges 51, 52 respectively with side walls 68, 69. The side walls 68, 69 have sharp cutting edges 68A, 69A proximally. The side wall 69 has a plurality of teeth 70 forming a rasping surface 71. This rasping surface 71 is helpful in revision cases as it cuts away excess bone as the surgeon taps or hammers the trial prosthesis 10 onto the distal femur F until the trial 10 reaches the position in FIG. 7. Surface 69 is provided with rasping surface 71 because it is the surface that will likely engage excess bone due to the angle 66 of inclination of connector 60 (and its attached stem extension 74, 75 or 76) with respect to plane 65.

The following is a list of suitable parts and materials for the various elements of the preferred embodiment of the present invention.

PARTS LIST

| Part Number | Description |
| --- | --- |
| 10 | femoral trial apparatus |
| 11 | trial body |
| 12 | distal surface |
| 13 | anterior surface |
| 14 | condylar surface |
| 15 | condylar surface |
| 16 | cutting edge |
| 17 | cutting edge |
| 18 | flat surface |
| 19 | flat surface |
| 20 | flat surface |
| 21 | flat surface |
| 22 | flat surface |
| 23 | recess |
| 23A | recess portion |
| 23B | recess portion |
| 24 | opening |
| 25 | opening |
| 26 | open space |
| 27 | groove |
| 28 | flat surface |
| 29 | flat surface |
| 30 | side wall |
| 31 | side wall |
| 32 | hole |
| 33 | hole |
| 34 | post |
| 34A | cutting guide |
| 34B | cutting guide |
| 35A | cutting guide |
| 35B | cutting guide |
| 36A | cutting guide |
| 36B | cutting guide |
| 37 | raised portion |
| 38 | raised portion |
| 39 | flat wall section |
| 40 | flat wall section |
| 41 | flat wall section |
| 42 | threaded fastener |
| 43 | flat surface |
| 44 | threaded fastener |
| 50 | module |
| 51 | flange |
| 52 | flange |
| 53 | opening |
| 54 | opening |
| 55 | lower end portion |
| 56 | flat surface |
| 57 | flat surface |
| 58 | anterior flat surface |
| 60 | stem |
| 61 | flat surface |
| 62 | frustroconical surface |
| 63 | transition section |
| 64 | cylindrical section |
| 65 | plane |
| 66 | angle |

PARTS LIST -continued

| Part Number | Description |
| --- | --- |
| 67 | central axis of stem |
| 68 | side wall |
| 68A | cutting edge |
| 69 | side wall |
| 69A | cutting edge |
| 70 | rasp teeth |
| 71 | rasping surface |
| 72 | U-shaped slot |
| 73 | U-shaped slot |
| 74 | stem extension |
| 75 | stem extension |
| 76 | stem extension |
| 77 | trial wedge |
| 78 | trial coupler |
| 79 | projecting threaded portion |
| 80 | socket |
| 81 | threaded fastener |
| 82 | peg |
| A | anterior cut surface |
| AC | anterior chamfer cut surface |
| D | distal cut surface |
| PC | posterior chamfer cut surface |
| P | posterior cut surface |
| F | femur |

The foregoing embodiments are presented by way of example only; the scope of the present invention is to be limited only by the following claims.

We claim:

1. A posterior stabilized femoral trial apparatus for preparing a patient's femur to receive a posterior stabilized femoral prosthesis, comprising:
   a) a trial body that includes medial and lateral portions and proximal and distal portions, the distal portion having an articulating surface for articulating with a patient's tibial component;
   b) the articulating surface including anterior, distal and posterior condylar portions;
   c) the proximal surface including a plurality of flat intersecting surfaces;
   d) a module that fits the trial body at the proximal surface, the module including a rasping surface that extends longitudinally along a proximal to distal plane that is generally parallel to an anterior to posterior plane;
   e) the module being removably attachable to the trial body at the proximal surface.

2. The posterior stabilized femoral trial apparatus of claim 1 wherein the module has sharp edges proximally.

3. The posterior stabilized femoral trial apparatus of claim 1 wherein the module includes spaced portions that extend laterally to both medial and lateral sides of the trial body along a medial to lateral line.

4. The posterior stabilized femoral trial apparatus of claim 1 further comprising a slot on the distal surface that receives the module.

5. The posterior stabilized femoral trial apparatus of claim 1 further comprising cutting surfaces on the trial body at the condylar surfaces.

6. The posterior stabilized femoral trial apparatus of claim 1 further comprising a plurality of cutting guide slots extending from the proximal to the distal surface of the body.

7. The posterior stabilized femoral trial apparatus of claim 1 further comprising an opening in the trial body in between the condylar portions that extends anteriorly a partial distance toward the anterior portion of the trial body.

8. The posterior stabilized femoral trial apparatus of claim 1 further comprising an opening in the trial body in between the condylar portions that extends anteriorly a partial distance toward the anterior portion of the trial body and a transverse bar that spans between the condylar portions posteriorly of the opening.

9. The posterior stabilized femoral trial apparatus of claim 1 further comprising fasteners that enable the module to be attached to and removed from the trial body.

10. The posterior stabilized femoral trial apparatus of claim 1 wherein the module includes a flanged portion that engages the body and a projecting portion that extends away from the flanged portion along a proximal—distal line.

11. The posterior stabilized femoral trial apparatus of claim 10 wherein the module includes a flanged portion that engages the body and a projecting portion that extends away from the flanged portion along a proximal—distal line and the projecting portion includes a plurality of flat wall portions.

12. The posterior stabilized femoral trial apparatus of claim 10 wherein the wall portions carry the rasping surface.

13. The posterior stabilized femoral trial apparatus of claim 10 wherein the wall portions include a wall portion that carries the rasping surface.

14. The posterior stabilized femoral trial apparatus of claim 10 wherein the module has a stem portion thereon.

15. The posterior stabilized femoral trial apparatus of claim 14 wherein the flanged portion defines a plane and the module has a stem portion that forms an angle of less than 90 degrees (90°) with the plane of the flanged portion.

16. The posterior stabilized femoral trial apparatus of claim 13 wherein the rasping surface is on the lateral side of the module.

17. A posterior stabilized femoral trial apparatus for preparing a patient's femur to receive a posterior stabilized femoral prosthesis, comprising:
   a) a trial body that includes proximal and distal portions, the distal portion having a "J" shaped curved articulating surface for articulating with a patient's tibial component;
   b) the articulating surface including an anterior surface, a distal surface, and a posterior condylar surface;
   c) the proximal surface including at least one flat surface;
   d) a module that removably fits the trial body at the flat surface, the module including a plurality of wall portions extending away from the flat surface, one of the wall portions having a rasping surface thereon;
   e) a stem on the module for fitting a patient's femoral intramedullary canal;
   f) slots through the trial body having cutting guide surfaces for guiding a surgeons cutting blade for shaping the patient's femur;
   g) the posterior condylar surface having cutting surface for cutting the patient's femur at the condylar portions of the femur; and
   h) the module having proximal sharp cutting edges.

18. The posterior stabilized femoral trial apparatus of claim 17 further comprising a stem extension and wherein the stem extension are connectable at respective sockets and to projecting portions.

19. The posterior stabilized femoral trial apparatus of claim 17 wherein the module comprises a base having medial and lateral flanged portions for engaging the respective medial and lateral sides of the trial body.

20. The posterior stabilized femoral trial apparatus of claim 17 wherein the module comprises:
   a base having medial and lateral flanged portions;
   a plurality of walls extending from the base;
   a stem member mounted on the walls generally opposite the base;
   one of the walls having said rasping surface thereon;
   the walls carrying a plurality of sharp cutting edges; and
   the rasping surface extending from the base to a position next to the stem member.

21. The posterior stabilized femoral trial apparatus of claim 20 further comprising a slot on the trial body that receives the base portion of the module.

22. The posterior stabilized femoral trial apparatus of claim 20 further comprising a plurality of cutting guide slots extending from the proximal to the distal surface of the trial body.

23. The posterior stabilized femoral trial apparatus of claim 20 further comprising an opening in the trial body in between the condylar portions that extends anteriorly a partial distance toward the anterior portion of the trial body, and wherein the walls of the module generally surround the opening.

24. The posterior stabilized femoral trial apparatus of claim 20 wherein the flanged portions have openings therethrough and further comprising connectors for affixing the flanges portions to the trial body at the openings.

25. The posterior stabilized femoral trial apparatus of claim 20 wherein the module has an open center portion surrounded by the walls.

26. A femoral trial apparatus for preparing a patient's femur to receive a femoral prosthesis, comprising:
   a) a trial body that includes proximal and distal portions, the distal portion having a curved articulating surface for articulating with a patient's tibial component;
   b) the articulating surface including an anterior surface, a distal surface and a posterior condylar surface;
   c) a kit that includes a plurality of modules that each fit the trial body at the proximal surface, each module including a base portion that fits the proximal surface and a walled portion projecting from the base portion;
   d) each module being removably attachable to the trial body at the proximal surface;
   e) the posterior condylar surface having a cutting edge portion that can cut the patient's femur at the femoral condyles during surgical placement of the trial body on the patient's femur; and
   f) each module having sharp proximal cutting edges.

* * * * *